(12) United States Patent
Grundei et al.

(10) Patent No.: US 6,425,921 B1
(45) Date of Patent: Jul. 30, 2002

(54) SLIDING PARTNERS FOR ARTIFICIAL JOINT IMPLANTS

(75) Inventors: Hans Grundei, Lübeck (DE); Wolfram Thomas, Rome (IT)

(73) Assignee: Eska Implants GmbH & Co., Lübeck (DE)

( * ) Notice: Subject to any disclaimer, the term of this patent is extended or adjusted under 35 U.S.C. 154(b) by 0 days.

(21) Appl. No.: 09/569,730

(22) Filed: May 12, 2000

Related U.S. Application Data

(63) Continuation of application No. PCT/EP98/07087, filed on Nov. 6, 1998.

(30) Foreign Application Priority Data

Nov. 13, 1997 (DE) .......................................... 197 50 121

(51) Int. Cl.[7] ................ A61F 2/32; A61F 2/34
(52) U.S. Cl. .................. 623/22.15; 623/18.11
(58) Field of Search ..................... 623/18.11, 22.11, 623/22.13, 22.15, 22.4, 23.11, 23.12; 384/13

(56) References Cited

U.S. PATENT DOCUMENTS

| | | |
|---|---|---|
| 4,676,799 A | 6/1987 | Legrand |
| 4,840,631 A | 6/1989 | Mathys |
| 5,462,362 A * | 10/1995 | Yuhta et al. .................. 384/13 |
| 5,683,466 A | 11/1997 | Vitale |

FOREIGN PATENT DOCUMENTS

| | | | |
|---|---|---|---|
| DE | 25 01 080 A1 | 7/1976 | |
| DE | 93 04 038 U1 | 8/1993 | |
| DE | 43 36 932 A1 | 5/1995 | |
| DE | 44 23 020 A1 | 1/1996 | |
| DE | 43 36 932 C2 | 6/1996 | |
| DE | 44 42 424 C1 | 8/1996 | |
| EP | 0 373 011 A1 | 6/1990 | |
| EP | 0 827 726 A2 | 3/1998 | |
| GB | 1-322-68 * | 7/1973 | ............. 623/23.11 |
| GB | 1 349 987 A | 4/1974 | |
| GB | 1 527 498 | 10/1978 | |
| WO | WO 96/19162 | 6/1996 | |

* cited by examiner

*Primary Examiner*—David J. Isabella
(74) *Attorney, Agent, or Firm*—Akin, Gump, Strauss, Hauer & Feld, L.L.P.

(57) ABSTRACT

Pairs of partner elements for artificial joint implants have two-dimensional surface contact in which one joint part (1) rotates, rolls, slides or combines these in one movement relative to another joint part (2). A gap (10) is formed between the sliding partner elements for a film consisting of natural synovia fluid. The surface of at least one of the sliding partner elements has regularly positioned recesses (3) which serve as a reservoir for the synovia.

7 Claims, 3 Drawing Sheets

SLIDING PARTNERS FOR ARTIFICIAL JOINT IMPLANTS

CROSS REFERENCE TO RELATED APPLICATION

This Application is a continuation of International Application PCT/EP98/07087, filed Nov. 6, 1998, the disclosure of which is incorporated herein by reference.

BACKGROUND OF THE INVENTION

The present invention relates to a two-dimensional pairing of sliding partners for artificial joint implants, in which a joint element executes a motion, which can be a rotating, rolling or sliding motion or a combination of these, relative to another joint element.

Such artificial joint implants are primarily artificial hip joints, knee joints, shoulder joints, and ankle joints. In general, however, the invention can be used with all artificial joints in which two sliding partners meet with each other.

Generally, one strives to keep the friction as low as possible between two joint elements moving relative to each other. A positive side effect of this is that particle abrasion becomes significantly less with a decreasing coefficient of friction, which benefits the long-term stability of the implant.

After the implantation of the artificial joints, the joint elements are wet by natural joint fluid, the so-called synovia. With joint elements processed for an exact fit, for example joint balls and joint cavities of an artificial hip joint, it can occur that the liquid film between the mutually moving joint elements can wear off and no longer exert any sort of lubricating function. The friction between the joint elements thereby abruptly and significantly increases, whereby the functioning capacity of the artificial joint is impaired, and the abrasion of particles from the sliding partners is fostered. Significant problems with respect to long-term retention of the implant in the patient's body thereby result.

In the prior art according to British patent specification 1 527 498, solving this problem has already been proposed. Thus, for example, on the boundary surface between the sliding partner in an artificial acetabulum and the artificial hip joint head, depressions are provided in the form of mutually interconnecting channels, in which the bodily fluid should provide for the lubrication of the joint. Quite similar constructions have been made known from German patent 43 36 932 and German published patent application 44 23 020. Due to the fact that the fluid-conducting channels communicate with one another, problems can arise with regard to some channels drying up at exposed points. The problem of uneven lubrication of the artificial hip joint then follows this drying up, whereby its functioning capacity is impaired in a negative manner.

From U.S. Pat. No. 5,462,363, abrasion-proof sliding partners are known, which should also find application in joint implants. Depressions are sunk into the surface of the joint elements, which provide a reservoir for the bodily fluid, which forms a liquid film between the mutually moving elements. The depressions here are generally formed throughout as cylindrical or blind holes. The problem here is that a buffering function of the bodily fluid is only insufficiently exerted in this regard. In the final analysis, this is a consequence of the pressure distribution due to the cylindrical construction of the depression. The synovia can therefore no longer execute its function reliably.

SUMMARY OF THE INVENTION

Against this background, the object of the present invention is to improve the above-described two-dimensional pairings of sliding partners for artificial joint implants, such that with high probability the liquid film of the synovia in the gap between the joint elements does not wear off, so that the synovia can reliably exert its function as joint lubricating fluid.

Accordingly, it is proposed that besides the gap for the synovia between the sliding partners, the surface of at least one sliding partner has regularly arranged depressions, which are carried out independently, thus without connection channels. The depressions in the surface of a sliding partner exert a collection function for the synovia, which in turn brings about a buffering action relative to the other sliding partner. The fluid-collecting function of the depressions ensures that a more or less abrupt onset of wearing off of the liquid film between the sliding partners cannot occur. It is constantly necessary to take care that the sliding partners do not directly roll against one another or slide on one another, but instead a film of synovia constantly reduces the friction between them. Fewer abrasion particles are the direct consequence, whereby the long-term stability of the implant is further improved.

The depressions are formed cup-shaped in cross section. In this way, they offer on the one hand a sufficiently large reservoir for the synovia, and on the other the possibility of a good wetting and exchange of the synovia stored in the depressions by the synovia flowing in afterward.

In accordance with one advantageous embodiment, it is provided that the depressions occupy up to 90% of the surface of at least one sliding partner. A relatively large volume of synovia is thereby quasi reserved in a reservoir, in order thus to attain the buffering effect.

The depressions can have a hexagonal opening, thus having in projection a honeycomb appearance. Alternatively thereto, the openings can also be formed round. The selection of one or another possibility depends, among other things, on the overall surface, the surface pressures to be expected, and upon the arrangement on the surface of the joint element in question.

According to a preferred embodiment, the depressions are arranged distributed in the surface of one sliding partner of that joint element which moves in relation to the other, stationary joint element. In other words, the depressions in this case are formed in the surface of the joint element, which executes the rolling on, rolling, rotation or sliding motion relative to the other joint element.

In the case of an artificial hip joint, the depressions would thus be provided in this embodiment on the joint ball, whereas the sliding partner in the acetabulum can be formed with a smooth surface.

The pairings of sliding partners are preferably selected from the group of material pairings: metal-metal, ceramic-ceramic, ceramic-metal, polyethylene-metal or polyurethane/ceramic compound-metal.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIG. 1b is a side view of an artificial joint ball of FIG. 1a;

FIG. 1c is a section view of the joint ball of FIG. 1b;

Hereinafter, functionally like parts are provided with the same reference numerals.

DETAILED DESCRIPTION OF THE INVENTION

Figure 1A:
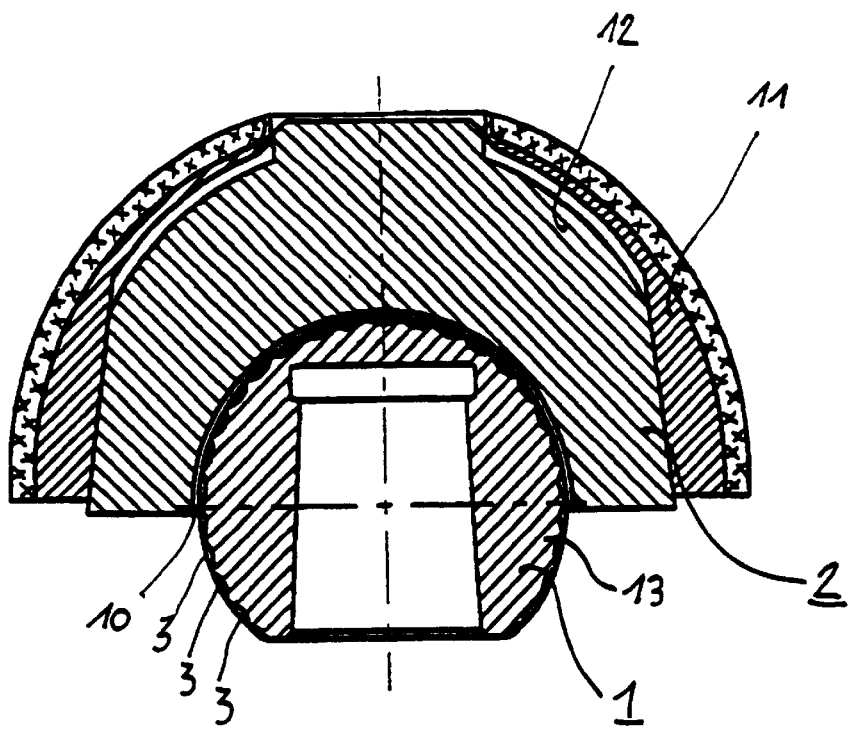
FIG. 1a is a side view through an artificial joint socket with inset, in which a joint ball rolls.

FIG. 1a provides a first overview. Shown therein is an artificial joint socket consisting of a metal base 11, which is set into the milled out acetabulum in the natural pelvis bone and is fixed there. The inset 12 serves as the sliding partner of the stationary joint element 2, which is fitted into the metal base 11. An artificial joint ball 13 engages into a cap or cup-shaped (hemispherical) recess in the inset 12 as movable joint element 1. Between the joint ball 13 and the cup-shaped recess in the inset 12, a gap 10 is formed, which is filled with synovia after the implantation. So that this liquid film does not wear off, whereby the joint would become dry, regularly arranged depressions 3 are provided on the surface of the joint ball 13, which are sunk into the surface. The depressions fill with synovia after the implantation and consequently form a reservoir for synovia, whereby it is assured that the liquid film in the gap 10 will not wear off.

Figures 1B, 1C:
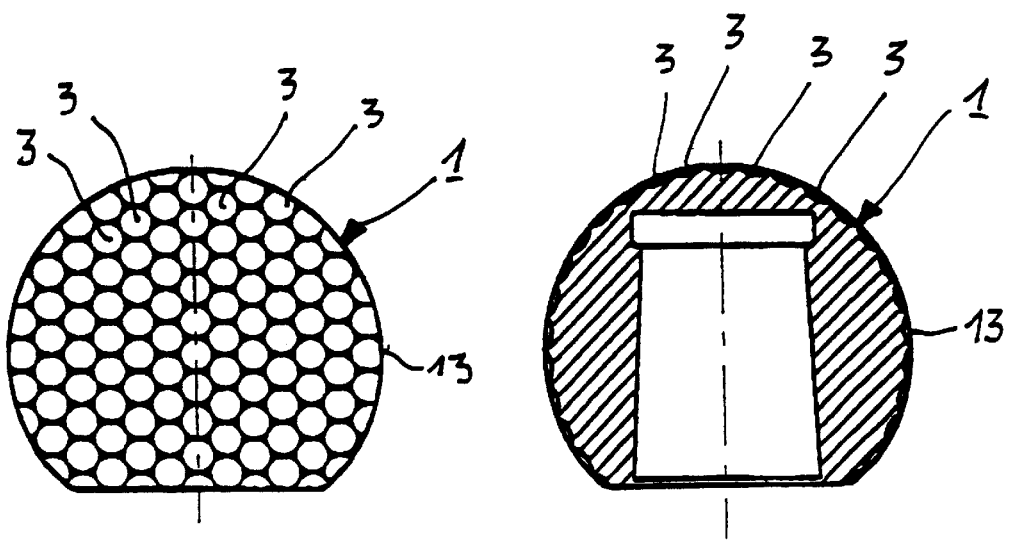

Which size areas the depressions 3 occupy on the surface of the joint ball 13 becomes quite visible from FIG. 1b, where a view of the joint ball 13 is shown. Up to 90% of the surface of the joint ball 13 is occupied by the depressions 3. The remaining surface parts form the actual rubbing surfaces with inset 12. In the embodiment represented, the openings of the depression are round. Alternatively, these can be formed hexagonally, wherein then the surface parts which actually roll in the cup in the inset 12 naturally change.

FIG. 1c shows the joint ball 13 once again in section and serves to round out the overall picture.

Figures 2A, 2B:
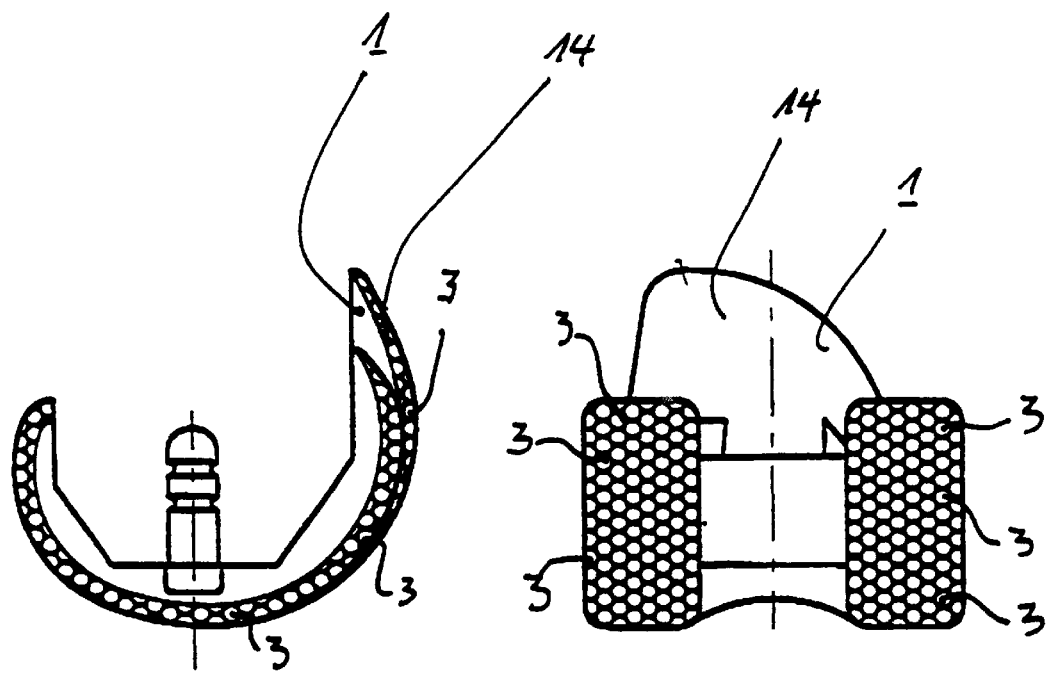
FIG. 2a is a side view of the femur condyle element of an artificial knee joint.
FIG. 2b is a view of the femur condyle element of FIG. 2a from a dorsal perspective.
Figure 2C:
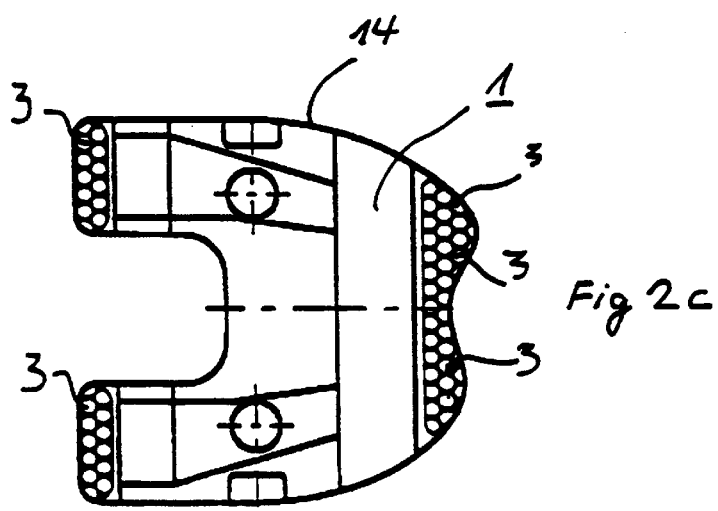
FIG. 2c is a view toward the femur condyle element according to FIGS. 2a and 2b.

In FIG. 2a a side view of a femur condyle element 14 of a first joint element 1 of an artificial knee joint is depicted. The condyles are here provided with depressions 3 all over. In particular, the rear condyles, as is apparent from FIG. 2b, are provided with depressions, since these assume the major portion in the rolling and sliding motion on the mating part of a tibia element (not shown) of the knee joint. FIG. 2c is the view toward the femur condyle element 14 from above, and rounds out the picture.

Figure 3A:
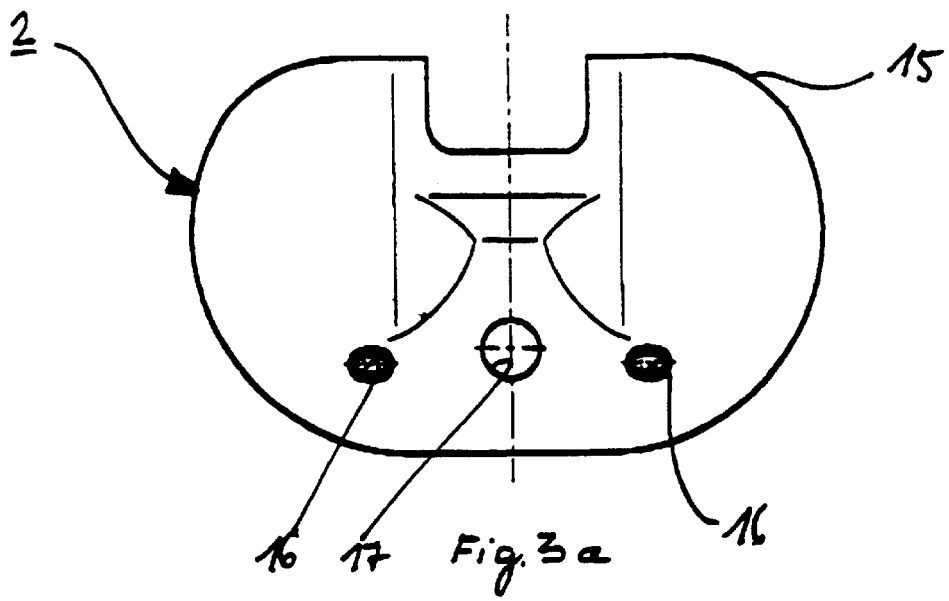
FIG. 3a is a view of a tibia plateau element of an artificial knee joint from below.

FIG. 3a shows a tibia plateau element 15 as a second (stationary) joint element 2 of an artificial knee joint viewed from below. Stated more precisely, the tibia plateau 15 forms the sliding partner of the second (stationary) joint element 2 of the tibia shaft element (not shown) of an artificial hip joint.

Figure 3B:
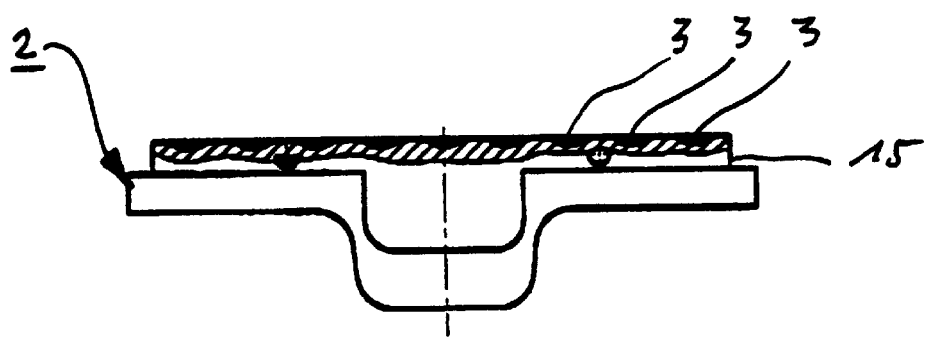
FIG. 3b is a section view through the tibia plateau.

The embodiment represented has an aperture 17, through which a rotation pin can engage. Openings 16 serve for passage of the synovia also into the intermediate space between the tibia shaft element (not shown) and the tibia plateau 15. This is apparent from FIG. 3b. In other words, the openings 16 provide for the passage of synovia to the tibia shaft element (not shown), in order to promote the floating mounting of the plateau 15 on the tibia shaft element. For this purpose, the rotation pin (not shown) engages through the aperture 17, so that the plateau 15 can move to a certain extent relative to the tibia shaft element. The upper side of the tibia plateau 15 facing the femur condyle element with smooth condyles, for example, is provided with depressions 3. Even here, the depressions serve as a reservoir for synovia, so that a sufficient fluid film is constantly provided between the tibia plateau with its slides and the femur condyle element.

Figure 3C:
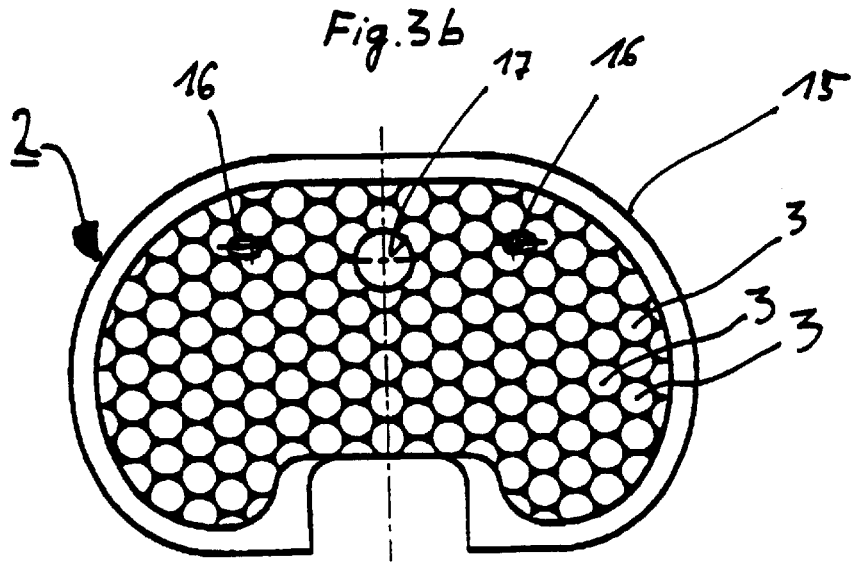
FIG. 3c is a plan view of the sliding paths of the tibia plateau according to FIGS. 3a and 3b.

The size density of the depressions 3 in the tibia plateau 15 on its surface is illustrated in FIG. 3c. The large number of depressions 3, which can occupy up to 90% of the entire surface of the sliding partner, provides for a correspondingly large supply of synovia in the depressions, and thereby for a sufficiently large inventory of synovia. The formation of the depressions 3 in this embodiment corresponds to that in the artificial hip joint according to FIGS. 1a to 1c.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. An artificial joint implant comprising first and second joint elements (1, 2) having respective mating surfaces, wherein the first joint element executes a rotating, rolling or sliding motion, or a combination of these motions, relative to the second joint element, the mating surfaces having a gap (10) therebetween for receiving a natural fluid film (synovia), and at least one of the mating surfaces having regularly arranged depressions (3) without mutual connection channels, the depressions having a concavely rounded cross-section perpendicular to the surface.

2. The artificial joint implant according to claim 1, wherein the depressions (3) occupy up to 90% of the surface of the at least one mating surface.

3. The artificial joint implant according to claim 1, wherein the depressions have a hexagonal opening.

4. The artificial joint implant according to claim 1, wherein the depressions have a round opening.

5. The artificial joint implant according to claim 1, wherein the first joint element (1) is movable, the second joint element is stationary, and the depressions (3) are arranged distributed on the mating surface of the first movable joint element.

6. The artificial joint implant according to claim 1, wherein the first and second joint elements are made of pairings of materials selected from the group consisting of metal-metal, ceramic-ceramic, ceramic-metal, polyethylene-metal, and polyurethane/ceramic compound-metal.

7. The artificial joint implant according to claim 1, wherein the depressions (3) are concavely dome-shaped.

* * * * *